US005744168A

United States Patent [19]
Fitzgerald

[11] Patent Number: 5,744,168
[45] Date of Patent: Apr. 28, 1998

[54] METHODS AND COMPOSITIONS FOR THE PREVENTION AND TREATMENT OF GASTROINTESTINAL DISORDERS

[75] Inventor: Jamesina Anne Fitzgerald, Hamilton, Ohio

[73] Assignee: The Procter & Gamble Company, Cincinnati, Ohio

[21] Appl. No.: 569,029

[22] Filed: Dec. 7, 1995

[51] Int. Cl.$^6$ ............................ A61K 33/24; A61K 31/65
[52] U.S. Cl. ...................... 424/653; 514/154; 514/199;
514/338; 514/370; 514/398; 514/400; 514/471;
514/925
[58] Field of Search ........................... 424/653; 514/154,
514/199, 338, 370, 398, 400, 471, 925

[56] References Cited

U.S. PATENT DOCUMENTS

| | | | |
|---|---|---|---|
| 4,049,817 | 9/1977 | Laber et al. | 424/270 |
| 4,514,421 | 4/1985 | Herschler | 418/110 |
| 5,196,205 | 3/1993 | Borody | 424/653 |
| 5,221,664 | 6/1993 | Berkowitz et al. | 514/6 |
| 5,256,684 | 10/1993 | Marshall | 514/398 |
| 5,407,688 | 4/1995 | Place | 424/653 |
| 5,476,669 | 12/1995 | Borody | 424/653 |

FOREIGN PATENT DOCUMENTS

| | | | |
|---|---|---|---|
| 462631 | 12/1991 | European Pat. Off. | |
| 962163 | 6/1950 | France | |
| 63-174926 | 7/1988 | Japan | A61K 31/29 |
| WO 92/01457 | 2/1992 | WIPO | A61K 33/24 |
| WO 95/32720 | 12/1995 | WIPO | A61K 33/24 |

OTHER PUBLICATIONS

Chevalier, C., et al., "Bilan Des Antiparasitaires A Usage Veterinaire: Antihelminthiques, Anticoccidiens, Antifongiques, Ectoparasiticides"(translation attached), Laboratory of Therapeutic Chemistry, College of Pharmacy, 37042 Tours Cedex, pp. 624–630 (1970).
DuPont, H., et al., Symptomatic Treatment of Diarrhea With Bismuth Subsalicylate Among Students Attending a Mexican University, Gastroenterology, vol. 73, (1977), pp. 715–718.
DuPont, H., "Enteropathogenic Organisms: New Etiologic Agents and Concepts of Disease", Medical Clinics of North America, vol. 62, No. 5 (1978), pp. 945–960.
Wolfe, M., "The Treatment of Intestinal Protozoan Infections", Medical Clinics of North America, vol. 56, No. 3 (1982), pp. 707–720.
Journal of the American Medical Association, "Travelers' Diarrhea", vol. 253, No. 18 (1985), pp. 2700–2704.
DuPont, L., "Nonfluid Therapy and Selected Chemoprophylaxis of Acute Diarrhea", The American Journal of Medicine, vol. 78, Suppl. 6B (1985), pp. 81–90.
Johnson, P., et al., "Comparison of Loperamide With Bismuth Subsalicylate for the Treatment of Acute Traveler's Diarrhea", The Journal Of the American Medical Association, vol. 255, No. 6 (1986), pp. 757–760.
Steffen, R., "Anerkannte Prinzipien zur Prophylaxe und Therapie der Reisediarrhoe", Schweiz. med. Wschr. 166, Nr. 20 (1986), pp. 670–673 (translation provided).
DuPont, H., et al., "Prevention of Travelers' Diarrhea By the Tablet Formulation of Bismuth Subsalicylate", The Journal of the American Medical Association, vol. 257, No. 10 (1987), pp. 1347–1350.
White, N., "Drug Treatment and Prevention of Malaria", European Journal of Clinical Pharmacology, vol. 34 (1988), pp. 1–14.
D'Alessandro, A., "Amebiasis Then", American Journal of Tropical Medicine and Hygiene, vol. 41, No. 3, Suppl. (1989), pp. 38–39.
Steffen, R., "Worldwide Efficacy of Bismuth Subsalicylate in the Treatment of Travelers' Diarrhea", Reviews of Infectious Diseases, vol. 12, Suppl. 1 (1990), pp. S80–S86.
Long, E., et al., "Alga Associated with Diarrhea in Patients with Acquired Immunodeficiency Syndrome and in Travelers", Journal of Clinical Microbiology, vol. 28, No. 6 (1990), pp. 1101–1104.
Wolfe, M., "Acute Diarrhea Associated With Travel", The American Journal of Medicine, vol. 88, Suppl. 6A (1990), pp. 34S–37S.
Qadri, S.M.H., "Infectious Diarrhea: Managing a Misery that is Still Worldwide", Postgraduate Medicine, vol. 88, No. 5 (1990), pp. 169–184).
Farthing, M.J.G., et al., "Treatment and Prevention of Travellers' Diarrhoea", Gastroenterology International, vol. 5, No. 3 (1992), pp. 162–175.
Zinsser Microbiology, 20th ed., Appleton & Lange (1992), pp. 1161–1173.
Arduino, R., et al., "Travellers' Diarrhoea", Bailliere's Clinical Gastroenterology, vol. 7, No. 2, (1993), pp. 365–385.
Chak, A., et al., "Traveler's Diarrhea", Gastroenterology Clinics of North America, vol. 22, No. 3 (1993), pp. 549–561.
American Health Consultants, "Cryptosporidiosis in Milwaukee", vol. 12, No. 15 (1993), pp. 113–115.
Wittner, M., et al., "Parasitic Infections in AIDS Patients: Cryptosporidiosis, Isosporiasis, Microsporidiosis, Cyclosporiasis", Infectious Disease Clinics of North America, vol. 7, No. 3 (1993), pp. 569–586.

(List continued on next page.)

*Primary Examiner*—Kevin E. Weddington
*Attorney, Agent, or Firm*—Mary Catherine Poland; Douglas C. Mohl; Jacobus C. Rasser

[57] ABSTRACT

The subject invention encompasses methods for prevention and treatment of a human or lower animal subject having a gastrointestinal disorder caused or mediated by algae and/or cyanobacteria comprising administering to the subject bismuth and one or more antimicrobials. The subject invention also encompasses compositions comprising bismuth and one or more antimicrobials for the prevention and treatment of a human or lower animal subject having a gastrointestinal disorder caused or mediated by algae and/or cyanobacteria.

16 Claims, No Drawings

OTHER PUBLICATIONS

Weber, R., et al., "Disseminated Microsporidiosis Due to *Encephalitozoon hellem:* Pulmonary Colonization, Microhematuria, and Mild Conjunctivitis in a Patient with AIDS", Clinical Infectious Diseases, vol. 17 (1993), pp. 415–419.

Kuhls, T., "Protozoal Infections of the Intestinal Tract in Children", Advances in Pediatric Diseases, vol. 8 (1993), pp. 177–202.

Scott, D., et al., "Treatment of Gastrointestinal Infections", Bailliere's Clinical Gastroenterology, vol. 7, No. 2 (1993), pp. 477–499.

Martindale, The Extra Pharmacopoeia, "Gastro–intestinal Agents", Thirtieth Ed., The Pharmaceutical Press (1993), p. 872.

Health, "Are Milwaukee–Type Parasites Floating in My Drinking Water?" (1993), p. 14.

Sun, T., et al., "Intestinal Microsporidiosis: Report of Five Cases", Annals of Clinical and Laboratory Science, vol. 24, No. 6 (1994), pp. 521–532.

American Drug Index, 38th Ed. (1994), pp.568–569.

Upcroft, P., "Multiple Drug Resistance in the Pathogenic Protozoa", Acta Tropica, vol. 56 (1994), pp. 195–212.

Herwaldt, B. et al., "Infections with Intestinal Parasites in Peace Corps Volunteers in Guatemala", Journal of Clinical Microbiology (1994), pp. 1376–1378.

Physicians' Desk Reference, 48th Ed. (1994), pp. 724–726.

Jernigan, et al., "Parasitic Infections of the Small Intestine", Gut, vol. 35, No. 3 (1994), pp. 289–293.

Fritsche, T., et al., "Introduction to Diagnostic Parasitology: Biologic, Clinical, and Laboratory Considerations", Manual of Clinical Microbiology, Sixth Ed., ASM Press (1995), pp. 1141–1144.

Cavier, R., "Etude des propriérés parasiticides de quelques complexes bismuthiques de l'oxy–8 quinoléine", Annales pharmaceutiques francaises, 1973, 31, No. 4, pp. 173–178 (translation attached).

Pitlik, S., et al., "Cryptosporidial Cholecystitis", The New England Journal of Medicine, vol. 308, No. 16 (Apr. 21, 1983), p. 967.

Than, U Pe, et al., "The Alkaloids of Holarrhena Antidysenterica", Union of Burma Journal of Science and Technology, vol. 2, Dec. 1969, pp. 423–436.

METHODS AND COMPOSITIONS FOR THE PREVENTION AND TREATMENT OF GASTROINTESTINAL DISORDERS

BACKGROUND OF THE INVENTION

While bacteria and viruses have long been recognized as a leading cause of diarrhea and other gastrointestinal illness throughout the world, it was not until recently that cyanobacteria and algae have been considered in the etiology. Algal blooms are occurring more often than before both in freshwater and coastal areas due to human-made changes in the environment. *Encyclopedia of Microbiology*, vol. 1, 68, (1992). Some of the bloom-forming algae produce toxic substances. These algae, which are ingested by mollusks and fish, may produce serious or even life-threatening illness when the fish and shellfish are consumed by humans. Id. In addition, species of cyanobacteria are becoming increasingly suspect for causing diarrhea and other gastrointestinal illness in healthy and immunocompromised subjects. Therefore, diarrhea and other gastrointestinal disorders associated with algae and/or cyanobacteria represent a serious health concern and the need for effective treatment therapies continues to grow.

It has been discovered by the present invention that the administration of bismuth salts and one or more antimicrobials may be effective for the prevention and/or treatment of gastrointestinal disorders caused or mediated by one or more organisms selected from the group consisting of algae, cyanobacteria, and combinations thereof. Thus, an object of the present invention is to provide safe and effective compositions and methods for preventing and/or treating gastrointestinal disorders caused or mediated by algae and/or cyanobacteria. A further object of the invention is to provide such a method comprising the administration of bismuth and one or more antimicrobials.

These and other objects of the present invention will become readily apparent from the detailed description which follows.

SUMMARY OF THE INVENTION

The present invention relates to a method for treatment of a human or lower animal subject having a gastrointestinal disorder caused or mediated by one or more organisms selected from the group consisting of algae, cyanobacteria, and combinations thereof, comprising administering to the subject from about 50 milligrams to about 5000 milligrams of bismuth, per day, for from about 1 to 56 days; and from about 100 milligrams to about 10,000 milligrams of each of one or more antimicrobials, per day, for from about 1 to about 21 days.

The present invention also relates to a method of prevention in a human or lower animal for a gastrointestinal disorder caused or mediated by one or more organisms selected from the group consisting of algae, cyanobacteria, and combinations thereof, comprising administering to the subject from about 50 milligrams to about 5000 milligrams of bismuth, per day, for from about 1 to 21 days; and from about 100 milligrams to about 10,000 milligrams of each of one or more antimicrobials, per day, for from about 1 to about 14 days.

DETAILED DESCRIPTION OF THE INVENTION

The methods of the present invention comprise the prevention and/or treatment of gastrointestinal disorder caused or mediated by one or more alga and/or cyanobacteria. Such gastrointestinal disorders are prevented and/or treated by the administration of bismuth and one or more antimicrobials. The components of the present invention are more fully defined below.

Gastrointestinal Disorder

The term "gastrointestinal disorder", as used herein, encompasses any infection, disease or other disorder of body, typically the upper and/or lower gastrointestinal tract, caused or mediated by one or more organisms selected from the group consisting of algae, cyanobacteria, and combinations thereof. Such disorders include one or more of the following conditions: diarrhea, abdominal pain and/or cramping, flatulence, nausea, abdominal distention, fever, constipation, blood, mucus and/or pus present in feces, vomiting, gastroenteritis, weight loss, anorexia, malaise, and any other condition commonly associated with infection by algae and/or cyanobacteria.

In immunocompromised subjects and children, gastrointestinal disorders caused or mediated by algae and/or cyanobacteria may be more severe and life threatening than the common disorders listed above. Therefore, the term "gastrointestinal disorder" also includes any condition commonly associated with algal and/or cyanobacterial infection in immunocompromised subject and children, including but not limited to, acute diarrhea, dehydration, electrolyte imbalance, colitis, and fatal necrosis of the intestine.

Algae and Cyanobacteria

Algae represent a large, heterogeneous group of primitive photosynthetic organisms which occur throughout all types of aquatic habitats and moist terrestrial environments. Nadakavukaren et al., *Botany, An Introduction to Plant Biology*, 324–325, (1985). The term "algae", as used herein, refers to the following algal divisions: Chlorophyta (green algae), Euglenophyta (euglenoids), Chrysophyta (golden and yellow-green algae, diatoms), Phaeophyta (brown algae), Pyrrophyta (dinoflagellates), and Rhodophyta (red algae). Such divisions are described more fully in Nadakavukaren et al., *Botany, An Introduction to Plant Biology*, 324–349, (1985), Brock et al., *Biology of Microorganisms*, 815–817,(1991), and Bold et al., *Introduction to the Algae*, 1–32,(1978), which are incorporated herein by reference.

Green algae include Chlorella and Chlorococcum. Euglenoids include Euglena mesnili, *Trachelomonas armata*, and *Phacus pleuronectes*. Golden algae include Dinobryon, spp. and Synura, spp. Diatoms include *Nitzschia pungens, f. maltiseries*, and *Nitzschia pseudodelicatissima*. Brown algae include *Pilayella littoralis* (zoospores). Dinoflagellates include *Dinophysis acuminata, Dinophysis norvegica*, Gymnodinium, and *Gonyaulax catenella*. Red algae include Rhodymenia, spp. and Bangia, spp. Preferred algae are Chlorophyta such as Chlorella and Chlorococcum; Chrysophyta such as Dinobryon and Synura; and combinations thereof. Most preferred algae are Chlorophyta such as Chlorella and Chlorococcum.

The term "cyanobacteria", as used herein, refers to prokaryotic organisms formerly classified as the blue-green algae. Cyanobacteria are a large and diverse group of photosynthetic bacteria which comprise the largest subgroup of Gram-negative bacteria. Cyanobacteria were classified as algae for many years due to their ability to perform oxygen-evolving photosynthesis. Curtis, "Cyanobacteria, Molecular Genetics", *Encyclopedia of Microbiology*, vol. 1, 627 (1992). While many cyanobacteria have a mucilaginous sheath which exhibits a characteristic blue-green color, the sheaths in different species may also exhibit colors including light gold, yellow, brown, red, emerald green, blue, violet, and blue-black. Raven et al., *Biology of Plants*, Fourth Edition, 183–185,(1986), included herein by reference. Cyanobacteria include *Microcystis aeruginosa, Trichodesmium erythraeum, Aphanizomenon flos-aquae*, and *Anabaena flos-aquae*.

Diagnosis of gastrointestinal disorders caused or mediated by algae may be accomplished by any method commonly used in the medical community.

Bismuth

The methods of treatment and/or prevention in the present invention involve administration of bismuth. As used herein, the quantity of bismuth is by weight of elemental bismuth.

The preferred duration of bismuth administration will vary according to the specific gastrointestinal disorder to be treated and the physical condition of the subject being treated. In general, as a method of treatment, bismuth may be administered in an amount of from about 50 milligrams to about 5000 milligrams, and preferably from about 50 milligrams to about 2500 milligrams, per day, for from about 1 to about 56 days, preferably for from about 2 to about 28 days, and most preferably for from about 7 to about 21 days.

In general, as a method of prevention, bismuth may be administered in an amount of from about 50 milligrams to about 5000 milligrams, and preferably from about 50 milligrams to about 2500 milligrams, per day, for from about 1 to about 21 days, and preferably for from about 1 to about 14 days. In a method of prevention, bismuth may be administered prior to potential exposure to algae and/or cyanobacteria. Such administration of bismuth may vary depending on the likelihood of algae and/or cyanobacteria exposure and condition of the subject and may be commenced at any time deemed beneficial by the medical community including from about 1 to about 7 days, from about 2 to about 5 days, and from about 3 to about 4 days, prior to potential exposure.

In the present invention, the term "bismuth", as used herein, includes bismuth in the form of a pharmaceutically-acceptable salt, bismuth or bismuth salt in the form of an organic or other complex which contains bismuth as an active ingredient, and mixtures thereof. Such organic complexes include 2,2'-spirobi[1,3,2,-benzodoxabismole]. Preferably, bismuth is administered in the present methods as a pharmaceutically-acceptable salt. Such bismuth salts include bismuth aluminate, bismuth subcarbonate, bismuth subcitrate, bismuth citrate, tripotassium dicitrato bismuthate, bismuth subgalate, bismuth subnitrate, bismuth tartrate, bismuth subsalicylate, and mixtures thereof. Bismuth citrate, bismuth subcitrate, tripotassium dicitrato bismuthate, bismuth tartrate, bismuth subsalicylate, and mixtures thereof are preferred bismuth salts for use in this invention.

The bismuth useful herein may be administered alone, or in combination with other pharmaceutically-acceptable components in a bismuth-containing composition. A variety of such compositions containing bismuth salts are commercially available. Such compositions include DeNol, containing tripotassium dicitrato bismuthate (by Brocades); Bislumina, containing bismuth aluminate (by Mazuelos); Roter, containing bismuth subnitrate (by Roterpharma); Devrom®, containing bismuth subgalate (by The Parthenon Co., Inc.); and Pepto-Bismol®, containing bismuth subsalicylate (by The Procter & Gamble Company).

As used herein, the term "administering" refers to any method which, in sound medical practice delivers the compounds or compositions used in this invention to the subject to be treated in such a manner so as to be effective in the treatment of the gastrointestinal disorder. Preferably, the bismuth is administered orally.

Antimicrobial

The present invention also include administration of a safe and effective amount of one or more antimicrobials, per day. As used herein, the term "antimicrobial(s)" refers to one or more antimicrobials.

Typically, according to the present methods for prevention and treatment, each of the one or more antimicrobials is administered at a level of from about 100 milligrams to about 10,000 milligrams, per day, for from about 1 to about 28 days. Preferably, each of the one or more antimicrobials is administered at a level of from about 100 milligrams to about 8000 milligrams per day, and more preferably at from about 100 milligrams to about 5000 milligrams per day. It is also preferred that each of the antimicrobials is administered for from about 1 to about 7 to 10 days, more preferably for from about 1 to about 14 days, and most preferably for from about 1 to about 21 days. In the methods for prevention, it is further preferred that each of the one or more antimicrobials is administered for from about 1 to about 14 days, and preferably for from about 1 to about 7 to 10 days.

The specific dosage of antimicrobial(s) to be administered, as well as the duration of antimicrobial(s) treatment, are mutually dependent, and will also depend upon such factors as the specific antimicrobial used, the number of antimicrobials used in the treatment, the resistance pattern of the infecting organism to the antimicrobial used, the ability of the antimicrobial to reach minimum inhibitory concentrations at the site of the infection, the nature and extent of other infections (if any), the personal attributes of the subject, compliance with the treatment regimen, and the presence and severity of any side effects of the treatment. Therefore, in the case of prevention or treatment with more than one antimicrobial, the duration of administration should depend on the type of antimicrobial rather than the administration of the antimicrobials for the same number of days.

A wide variety of antimicrobials are useful in this invention. As used herein, the term "antimicrobial" refers to any naturally-occurring, synthetic or semi-synthetic compound or composition or mixture thereof, which is safe for human use as used in the methods of this invention, and is effective in killing or substantially inhibiting the algae and/or cyanobacteria when used in the methods of this invention. Antiprotozoal agents, antiparasitic agents and antibiotics are among the preferred antimicrobials useful herein.

Antiprotozoal and antiparasitic agents suitable for use in the present invention include any of the agents recognized in the medical community as acceptable for treating protozoal infection. Such antiprotozoal and antiparasitic agents include atovaquone, chloroquine phosphate, quinacrine hydrochloride, iodoquinol, pyrimethamine, and mefloquine hydrochloride.

Antibiotics can be generally classified by chemical composition, into the following principal groups: the aminoglycosides, such as gentamicin, neomycin, kanamycin, and streptomycin; the macrolides, such as erythromycin, clindamycin, and rifampin; the penicillins, such as penicillin G, penicillin V, ampicillin and amoxycillin; the polypeptides such as bacitracin and polymyxin; the tetracyclines such as tetracycline, chlortetracycline, oxytetracycline and doxycycline; the cephalosporins such as cephalexin and cephalothin; quinolones such as ciprofloxacin, norfloxacin and ofloxacin; and such miscellaneous antibiotics as trimethoprim, sulfamethoxazole and the combination thereof, and chloramphenicol. These antibiotics can generally be said to function in one of four ways: inhibition of cell wall synthesis, alteration of cell wall permeability, inhibition of protein synthesis or inhibition of nucleic acid synthesis.

Other antimicrobials useful herein include the sulfonamides; nitrofurans, such nitrofurazon, nitrofurantoin, and furozolidone; metronidazole, tinidazole, and nimorazole. Antimicrobials among those useful herein are described in *Remington's Pharmaceutical Sciences*, 18th Edition, pp. 1173–1232 (1990), which is incorporated herein by reference.

While any of these antimicrobials may be used, penicillin, tetracycline, metronidazole, doxycycline, tinidazole, amoxycillin, ampicillin, nitrofurantoin, and atovaquone are among the preferred antimicrobials for use in the present invention.

As stated above, the specific preferred quantity of antimicrobial and duration of treatment used in the methods of this invention will, in addition to other factors, depend upon the particular antimicrobial used and its pharmacology. In general, though, the tetracyclines are preferably administered at a level of from about 100 milligrams to about 2,000 milligrams per day. Macrolides (such as erythromycin) are preferably administered at a level of from about 1,000 milligrams to about 4,000 milligrams per day. Penicillins are preferably administered at a level of from about 500 milligrams to about 3,000 milligrams per day. The aminoglycosides (such as neomycin) are preferably administered at a level of from about 100 milligrams to about 8,000 milligrams per day. Nitrofurans (such as nitrofurantoin) are administered preferably at levels of from about 100 milligrams to about 800 milligrams per day. Preferably, metronidazole is administered at a level of from about 375 or 500 to about 2,000 milligrams per day. Preferably, atovaquone is administered at a level of from about 750 to about 2250 milligrams, per day.

The specific method of administering the antimicrobial, according to the processes of this invention, may depend upon such factors as the particular antimicrobial(s) used, the site of infection, the amount of antimicrobial(s) to be administered per day, the presence of any adverse side effects, and the interactions (if may) between the antimicrobial(s) and the bismuth. Thus, the antimicrobial(s) may be administered under the process of this invention by single daily doses, or by administration in two, three, four, or more doses per day.

Bismuth/Antimicrobial Compositions

The present invention also provides compositions for the treatment of gastrointestinal disorders comprising a safe and effective amount of bismuth and a safe and effective amount of one or more antimicrobials. Typically, these compositions comprise a safe and effective amount one or more antimicrobials; a safe and effective amount of bismuth; and pharmaceutically-acceptable carrier materials; wherein the safe and effective amount of the one or more antimicrobials and the bismuth is effective for preventing and/or treating a gastrointestinal disorder caused or mediated by one or more organisms selected from the group consisting of algae, cyanobacteria, and combinations thereof.

A preferred composition comprises:
(a) from about 50 milligrams to about 5,000 milligrams of bismuth; and
(b) from about 100 milligrams to about 10,000 milligrams of each of one or more antimicrobials.

Preferably, the bismuth salt is present at a level of from about 50 milligrams to about 2500 milligrams. Also, preferably each of the one or more antimicrobials is present at a level of from about 100 milligrams to about 8000 milligrams.

The compositions of the present invention may contain optional components which affect the physical and therapeutic characteristics of the present compositions. In particular, a variety of pharmaceutically-acceptable carriers and excipients may be included, depending upon the particular dosage form to be used. Various oral dosage forms can be used, including such solid forms as tablets, capsules, granules and bulk powders. Tablets can be compressed, tablet triturates, enteric-coated, sugar coated, film-coated or multiple compressed, containing suitable binders, lubricants, diluents, disintegrating agents, coloring agents, flavoring agents, flow-inducing agents and melting agents. Liquid oral dosage forms include aqueous solutions, emulsions, suspensions, solutions, and/or suspensions reconstituted from non-effervescent granules and effervescent preparations reconstituted from effervescent granules, containing suitable solvents, preservatives, emulsifying agents, suspending agents, diluents, sweeteners, melting agents, coloring, and flavoring agents.

Specific examples of pharmaceutically-acceptable carriers and excipients that may be used to formulate oral dosage forms of the present invention are described in U.S. Pat. No. 3,903,297, Robert, issued Sep. 2, 1975, incorporated by reference herein. Techniques and compositions for making dosage forms useful herein are described in the following references, all incorporated by reference herein: 7 *Modern Pharmaceutics*, Chapters 9 and 10 (Banker and Rhodes, editors, 1979); Lieberman, et al., *Pharmaceutical Dosage Forms*: Tablets (1981); and Ansel et al., *Pharmaceutical Dosage Forms and Drug Delivery Systems*, Fifth Edition, 134–254,(1990).

The compositions of this invention may be used according to the methods of this invention by administering the composition from 1 to 7 times per day, and preferably from 1 to 4 times per day; for from 1 to 21 days, preferably for from about 1 to about 14 days. The specific frequency of administration will depend upon such factors as the specific bismuth compound or composition and antimicrobial(s) used, the levels at which the components are incorporated in the composition, the nature and severity of the condition to be treated, and the nature of any concurrent therapy, if any.

Administration

The present invention comprises methods wherein the administration of bismuth and the administration of one or more antimicrobials are performed simultaneously (beginning and ending on the same day), concurrently (overlapping), or consecutively (sequential, but wherein the course of the treatment is substantially continuous). Preferably, the step of administering the antimicrobial(s) is not commenced prior to commencing the step of administering bismuth.

As used herein, the term "administering" refers to any method which, in sound medical practice delivers the compounds or compositions used in this invention to the subject to be treated in such a manner so as to be effective in the treatment of the gastrointestinal disorder. Preferably, the bismuth is administered orally. Also preferably, the antimicrobial(s) is administered either orally, intravenously, or any other method which effects systemic distribution, or local distribution to the site of the gastrointestinal disorder, of the antimicrobial(s) in the subject. Oral ingestion of the antimicrobial(s) is a preferred method of administering the antimicrobial(s) in the methods of this invention.

The following non-limiting examples illustrate the methods and uses of the present invention.

EXAMPLE I

A young boy suffers from abdominal cramps and painful acute diarrhea, following a swim in his family's pond. Fecal samples are taken from the subject and analyzed microscopically and via culture. There are no indications of bacterial infection. Likewise, there are no indications of intestinal protozoa or worms. Strangely, large numbers of green algae, determined to be Chlorococcum, are evident in the diarrheic stools. The young boy is treated by administering a composition containing bismuth subsalicylate, sold by The Procter & Gamble Company under the name "Pepto-Bismol®". The composition, in liquid form, is administered four times daily, in equal doses delivering approximately 2500 milligrams of bismuth per day, for 21 days, and 100 milligrams of furolzolidone, four times daily, for about 10 days. After the completion of this regimen, fecal samples from the subject are analyzed again, finding no trace of algal infection. The patient remains asymptomatic, and another fecal analysis performed 5 months later is normal.

In the above example, tripotassium dicitrato bismuthate, bismuth tartrate, bismuth citrate, and bismuth subnitrate are substituted, respectively, for bismuth subsalicylate, with substantially similar results.

EXAMPLE II

An elderly couple report fever, vomiting, and explosive diarrhea the morning after an evening celebration at a local Japanese restaurant. Since the couple prefer a vegetarian diet and ate only a Porphyra and kelp salad, the traditional suspect, poorly cooked seafood, was ruled out. Wet mount analysis of the fecal samples, show large numbers of a tiny, non-motile, unicellular green alga, Chlorella. The infection is diagnosed and treated by concurrent administration of 750 milligrams of metronidazole, three times daily, for about 21 days and 25 milligrams of pyrimethamine in a tablet daily for the first 2 successive days. After two days (commencing on the third day) approximately 400 milligrams of bismuth in the form of bismuth subcitrate ("DeNol" sold by Brocades), is administered in four equal doses daily for about 28 days. Thereafter, fecal, samples from the subject are analyzed again, finding no trace of algal infection.

In the above example, atovaquone, chloroquine phosphate, iodoquinol, penicillin, erythromycin, nitrofuran, and tetracycline are substituted, respectively, for metronidazole or pyrimethamine, with substantially similar results. In addition, either antibiotic can be eliminated from the regimen (e.g., due to hypersensitivity) and maintain therapeutic efficacy. Bismuth citrate, bismuth tartrate, bismuth aluminate, bismuth subgalate, bismuth subsalicylate, and tripotassium dicitrato bismuthate are substituted, respectively, for bismuth subcitrate, with substantially similar results.

EXAMPLE III

A Peace Corps volunteer diagnosed with AIDS, prepared for a temporary assignment working at an AIDS hospice in Peru. The job description describes a small village with sub-standard sanitation and water purification systems. The people of the village had recently experienced an outbreak of dysentery attributed to the cyanobacterium, *Microcystis aeruginosa*. Before leaving for his new assignment, clinical results show no evidence of cyanobacterial infection. Before departure, the subject is given approximately 800 milligrams of bismuth, in the form bismuth subgalate (Devrom®, sold by The Parthenon Company, Inc.), in four equal doses daily, and 750 milligrams of nitrofurantoin daily for about 21 days. Upon returning to the U.S., approximately 30 days after the initial clinical analysis, the subject remains asymptomatic. Fecal samples from the subject are analyzed and no evidence of a cyanobacterial infection is found.

What is claimed is:

1. A method for treatment of a human or lower animal subject having a gastrointestinal disorder caused or mediated by one or more organisms selected from the group consisting of algae, cyanobacteria, and combinations thereof, comprising administering to the subject from about 50 milligrams to about 5000 milligrams of bismuth, per day for from about 1 to 56 days; and from about 100 milligrams to about 10,000 milligrams of each of one or more antimicrobials, per day, for from about 1 to about 28 days.

2. The method of claim 1 wherein the bismuth is administered at a level of from about 50 milligrams to about 2500 milligrams, per day.

3. The method of claim 2 wherein the bismuth is selected from the group consisting of bismuth aluminate, bismuth subcarbonate, bismuth subcitrate, bismuth citrate, tripotassium dicitrato bismuthate, bismuth subgalate, bismuth subsalicylate, bismuth tartrate, and mixtures thereof.

4. The method of claim 1 wherein each of the one or more antimicrobials is administered at a level of from about 100 milligrams to about 8000 milligrams, per day.

5. The method of claim 4 wherein the one or more antimicrobials are selected from the group consisting of penicillin, tetracycline, metronidazole, doxycycline, tinidazole, amoxycillin, ampicillin, nitrofurantoin, and atovaquone.

6. The method of claim 1 wherein the bismuth is administered for from about 2 to 28 days and the one or more antimicrobials are administered for from about 1 to about 21 days.

7. The method of claim 1 wherein the organisms are cyanobacteria selected from the group consisting of *Microcystis aeruginosa, Trichodesmium erythraeum, Anabaena flos-aquae, Aphanizomenon flos-aquae*, and combinations thereof.

8. A method for prevention in a human or lower animal subject in need therof, of a gastrointestinal disorder caused or mediated by one or more organisms selected from the group consisting of algae, cyanobacteria, and combinations thereof, comprising administering to the subject from about 50 milligrams to about 5000 milligrams of bismuth, per day, for from about 1 to about 21 days; and from about 100 milligrams to about 10,000 milligrams of each of one or more antimicrobials, per day, for from about 1 to about 14 days.

9. The method of claim 8 wherein the bismuth is administered at a level of from about 50 milligrams to about 2500 milligrams, per day.

10. The method of claim 9 wherein the bismuth is selected from the group consisting of bismuth aluminate, bismuth subcarbonate, bismuth subcitrate, bismuth citrate, tripotassium dicitrato bismuthate, bismuth subgalate, bismuth subsalicylate, bismuth tartrate, and mixtures thereof.

11. The method of claim 8 wherein each of the one or more antimicrobials is administered at a level of from about 100 milligrams to about 8000 milligrams, per day.

12. The method of claim 11 wherein the one or more antimicrobials are selected from the group consisting of penicillin, tetracycline, metronidazole, doxycycline, tinidazole, amoxycillin, ampicillin, nitrofurantoin, and atovaquone.

13. The method of claim 8 wherein the bismuth is administered for from about 1 to about 14 days and the one or more antimicrobials are administered for from about 1 to about 7 to 10 days.

14. The method of claim 8 wherein the organisms are algae and cyanobacteria selected from the group consisting of Chlorella, Chlorococcum, *Microcystis aeruginosa, Anabaena flos-aqua, Aphanizomenon flos-aquae*, and combinations thereof.

15. The method of claim 1 wherein the subject is administered a composition comprising:

(a) a safe and effective amount of bismuth;

(b) a safe and effective amount of one or more antimicrobials;

(c) pharmaceutically-acceptable carriers materials; and wherein the safe and effective amount of the bismuth and one or more antimicrobials is effective for treating the gastrointestinal disorder caused or mediated by one or more organisms selected from the group consisting of algae, cyanobacteria, and combinations thereof.

16. The method of claim 8 wherein the subject is administered a composition comprising:

(a) a safe and effective amount of bismuth;

(b) a safe and effective amount of one or more antimicrobials;

(c) pharmaceutically-acceptable carriers materials; and wherein the safe and effective amount of the bismuth and one or more antimicrobials is effective for preventing the gastrointestinal disorder caused or mediated by one or more organisms selected from the group consisting of algae, cyanobacteria, and combinations thereof.

* * * * *